US 7,857,866 B2

(12) United States Patent
Guerin

(10) Patent No.: US 7,857,866 B2
(45) Date of Patent: Dec. 28, 2010

(54) DYEING METHOD USING A COMPOSITION COMPRISING AN ORTHO-DIPHENOL AND COMPRISING A WIPING, DRYING OR NON RINSING STAGE

(75) Inventor: Frédéric Guerin, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/637,264

(22) Filed: Dec. 14, 2009

(65) Prior Publication Data

US 2010/0154138 A1 Jun. 24, 2010

Related U.S. Application Data

(60) Provisional application No. 61/141,420, filed on Dec. 30, 2008.

(30) Foreign Application Priority Data

Dec. 12, 2008 (FR) .................. 08 58554

(51) Int. Cl.
*A61Q 5/10* (2006.01)
(52) U.S. Cl. .............. 8/405; 8/406; 8/424; 8/435; 8/594; 8/629; 132/202; 132/208
(58) Field of Classification Search .......... 8/405, 8/406, 424, 435, 594, 629; 132/202, 208
See application file for complete search history.

(56) References Cited

U.S. PATENT DOCUMENTS

| 4,801,302 | A | 1/1989 | Grollier |
| 5,603,734 | A * | 2/1997 | Prota et al. ............ 8/424 |
| 6,953,486 | B2 | 10/2005 | Pruche |

| 2003/0103917 | A1 | 6/2003 | Pruche |

FOREIGN PATENT DOCUMENTS

| DE | 199 59 480 A1 | 6/2001 |
| DE | 10 2005 062 830 A1 | 1/2007 |
| EP | 0 124 393 A1 | 11/1984 |
| EP | 0 664 114 A1 | 7/1995 |
| FR | 2 598 318 A1 | 11/1987 |
| FR | 2 814 945 A1 | 4/2001 |
| FR | 2 814 946 A1 | 4/2001 |
| FR | 2 814 947 A1 | 4/2001 |
| FR | 2 814 943 A1 | 4/2002 |
| JP | 08 012539 | 1/1996 |

OTHER PUBLICATIONS

French Search Report for FR 0858554, dated Aug. 27, 2009.
French Search Report for FR 0858556, dated Aug. 19, 2009.
French Search Report for FR 0858557, dated Aug. 27, 2009.
French Search Report for FR 0858555, dated Aug. 19, 2009.
French Search Report for FR 0858558, dated Aug. 24, 2009.
English language abstract of DE 199 59 480 A1, Jun. 21, 2001.
English language abstract of DE 10 2005 062 830 A1, Jan. 4, 2007.
English language abstract of EP 0 124 393 A1, Jul. 11, 1984.
English language abstract of FR 2 814 943 A1, Apr. 12, 2002.
English language abstract of FR 2 814 945 A1, Apr. 12, 2002.
English language abstract of JP 08 012539, Jan. 16, 1996.
Co-pending Application filed Dec. 14, 2009.

* cited by examiner

*Primary Examiner*—Eisa B Elhilo
(74) *Attorney, Agent, or Firm*—Finnegan, Henderson, Farabow, Garrett & Dunner, L.L.P.

(57) ABSTRACT

The disclosure relates to methods for dyeing keratinous fibers by treatment of said fibers with i) at least entity chosen from ortho-diphenol and derivatives thereof, ii) at least one metal salt, iii) hydrogen peroxide or at least one system which generates hydrogen peroxide and iv) at least one (bi)carbonate, said method additionally involving an intermediate wiping and/or drying and/or non rinsing stage.

17 Claims, No Drawings

DYEING METHOD USING A COMPOSITION COMPRISING AN ORTHO-DIPHENOL AND COMPRISING A WIPING, DRYING OR NON RINSING STAGE

This application claims benefit of U.S. Provisional Application No. 61/141,420, filed Dec. 30, 2008. This application also claims benefit of priority under 35 U.S.C. §119 to French Patent Application No. 0858554, filed Dec. 12, 2008.

The present disclosure relates to compositions, methods, and kits for dyeing keratinous fibers, such as compositions, methods, and kits making use of i) at least one entity chosen from ortho-diphenol and derivatives thereof, ii) at least one metal salt, iii) at least hydrogen peroxide or one system which generates hydrogen peroxide and iv) at least one (bi)carbonate, the methods involving at least one intermediate wiping and/or drying stage and/or non rinsing stage.

So-called "permanent" colorings can be obtained with dyeing compositions comprising oxidation dye precursors, generally known as oxidation bases, such as ortho- or para-phenylenediamines, ortho- or para-aminophenols and heterocyclic compounds. These oxidation bases can be colorless or weakly colored compounds which, in combination with oxidizing products, can give rise, by an oxidative coupling process, to colored compounds. The shades obtained can be varied by combining these oxidation bases with couplers or coloring modifiers, the latter being chosen, e.g., from aromatic meta-diamines, meta-aminophenols, meta-diphenols and certain heterocyclic compounds, such as indole compounds. This oxidation dyeing method can involve applying, to the keratinous fibers, bases or a mixture of bases and of couplers with hydrogen peroxide ($H_2O_2$ or aqueous hydrogen peroxide solution) as oxidizing agent, allowing diffusion to occur, and then rinsing the fibers. The colorings which result therefrom can be permanent, powerful and resistant to external agents, e.g., to light, bad weather, washing operations, perspiration and rubbing actions.

However, the commercial hair dyes which comprise them can exhibit disadvantages, such as staining or problems of smell, of comfort or of decomposition of the keratinous fibers. This can be the case with, for example, oxidation dyeing operations.

There exists a need to develop dyeing methods which make it possible to obtain powerful colorings starting from ortho-diphenols, such as by starting from a natural extract rich in ortho-diphenols, while limiting the decoloration of the keratinous fibers. There further exists a need to obtain colorings which are less aggressive to the hair and, at the same time, which can withstand external agents (light, bad weather, shampooing operations) and which can be persistent and homogeneous while remaining powerful and chromatic. The subject matter of the present disclosure, inter alia, can in some embodiments satisfy one or more of these needs.

One aspect of the present disclosure is a multistage method for dyeing keratinous fibers, comprising:

a) treating said fibers, in at least two stages, with:
  i) at least one entity chosen from ortho-diphenol and derivatives thereof,
  ii) at least one metal salt,
  iii) hydrogen peroxide or at least one system which generates hydrogen peroxide, and
  iv) at least one (bi)carbonate; and b) at least one of mechanically wiping or drying the fibers, wherein the mechanical wiping or drying occurs between the first and last of the at least two treating stages, with the proviso that said method does not comprise a rinsing stage just before the stage of treating the fibers with the at least one (bi)carbonate.

Another aspect of the present disclosure is a multistage method for dyeing keratinous fibers, comprising a) treating said fibers, in at least two stages, with:
  i) at least one entity chosen from ortho-diphenol and derivatives thereof,
  ii) at least one metal salt,
  iii) hydrogen peroxide or at least one system which generates hydrogen peroxide, and
  iv) at least one (bi)carbonate; and b) mechanically wiping the keratinous fibers to remove excess material, at least once between the first and last of the at least two treating stages, said mechanical wiping occurring either after treating the fibers with ingredients i) and ii) and said excess material comprising ingredients i and ii, or after treating the fibers with ingredients i), ii), and iii), and said excess material comprising ingredients i), ii), and iii), with the proviso that said method does not comprise a rinsing stage just before the stage of treating the fibers with the at least one (bi)carbonate.

The methods according to the disclosure can exhibit the benefit of dyeing human keratinous fibers with powerful and chromatic colorings which can be resistant to washing operations, to perspiration, to sebum and to light and which can be in addition long lasting without a detrimental change to said fibers. Furthermore, the colorings obtained using the methods of the disclosure can give homogeneous colors from the root to the tip of a fiber (that is, they can have low dyeing selectivity).

i) Ortho-Diphenol Derivative(s):

The first ingredient used in the method according to the disclosure is i) at least one entity chosen from ortho-diphenol and derivatives thereof.

In some embodiments, the disclosure relates to an entity chosen from ortho-diphenol and derivatives thereof or a mixture of compounds comprising at least one aromatic ring, such as a benzene ring, comprising at least two hydroxyl (OH) groups carried by two adjacent carbon atoms of the aromatic ring. The ortho-diphenol derivative or derivatives according to the disclosure are not autoxidizable derivatives comprising an indole unit. For example, they can be other than 5,6-dihydroxyindole.

The aromatic ring can be a fused aryl ring or a fused heteroaromatic ring, i.e. a ring optionally comprising at least one heteroatom, such as benzene, naphthalene, tetrahydronaphthalene, indane, indene, anthracene, phenanthrene, isoindole, indoline, isoindoline, benzofuran, dihydrobenzofuran, chromane, isochromane, chromene, isochromene, quinoline, tetrahydroquinoline and isoquinoline, said aromatic ring comprising at least two hydroxyl groups carried by two adjacent carbon atoms of the aromatic ring. In some embodiments, the aromatic ring of the ortho-diphenol derivatives according to the disclosure is a benzene ring.

A "fused ring" is understood to mean that at least two saturated or unsaturated and heterocyclic or nonheterocyclic rings exhibit a common bond, i.e. that at least one ring is placed side by side with another ring.

The entity chosen from ortho-diphenol and derivatives thereof according to the disclosure may or may not be salified, i.e., present as a salt. It can also occur in the aglycone form (without bonded sugar) or in the form of a glycosylated compound.

In some embodiments, the ortho-diphenol derivative i) represents a compound of formula (I) or one of its oligomers, in or not in the salified form:

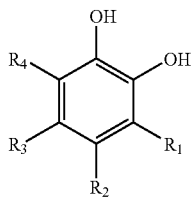

in which formula (I) the substituents:
$R_1$ to $R_4$, which can be identical or different, represent:
a hydrogen atom,
a halogen atom,
a hydroxyl radical,
a carboxyl radical,
an alkyl carboxylate or alkoxycarbonyl radical,
an optionally substituted amino radical,
an optionally substituted linear or branched alkyl radical,
an optionally substituted linear or branched alkenyl radical,
an optionally substituted cycloalkyl radical,
an alkoxy radical,
an alkoxyalkyl radical,
an alkoxyaryl radical, it being possible for the aryl group to be optionally substituted,
an aryl radical,
a substituted aryl radical,
a saturated or unsaturated heterocyclic radical which does or does not carry a cationic or anionic charge, which is optionally substituted and/or which is optionally fused with an aromatic ring, such as a benzene ring, said aromatic ring being optionally substituted, e.g., by at least one hydroxyl or glycosyloxy group,
a radical comprising at least one silicon atom;
or two of the substituents carried by two adjacent carbon atoms $R_1$-$R_2$, $R_2$-$R_3$ or $R_3$-$R_4$ form, together with the carbon atoms carrying them, a saturated or unsaturated, aromatic or nonaromatic, ring optionally comprising at least one heteroatom and optionally fused with at least one saturated or unsaturated ring optionally comprising at least one heteroatom. In some embodiments, $R_1$ to $R_4$ jointly form from one to four rings.

In some embodiments, the disclosure relates to ortho-diphenol derivatives of formula (I), two adjacent substituents $R_1$-$R_2$, $R_2$-$R_3$ or $R_3$-$R_4$ of which cannot form a pyrrolyl radical with the carbon atoms which carry them. In some embodiments, $R_2$ and $R_3$ cannot form a pyrrolyl radical fused to the benzene ring carrying the two hydroxyls.

The saturated or unsaturated and optionally fused rings can also be optionally substituted.

The alkyl radicals can be saturated and linear or branched hydrocarbon radicals, for example, $C_1$-$C_{20}$ radicals, $C_1$-$C_{10}$ radicals, or $C_1$-$C_6$ alkyl radicals, such as methyl, ethyl, propyl, butyl, pentyl and hexyl.

The alkenyl radicals can be unsaturated and linear or branched $C_2$-$C_{20}$ hydrocarbon radicals, which in some embodiments comprise at least one double bond, such as ethylene, propylene, butylene, pentylene, 2-methylpropylene and decylene.

The aryl radicals can be mono- or polycyclic (which may or may not be fused) carbon-comprising radicals which in some embodiments comprise from 6 to 30 carbon atoms and have at least one ring which is aromatic; a phenyl, biphenyl, naphthyl, indenyl, anthracenyl and tetrahydronaphthyl is in some embodiments chosen as the aryl radical.

The alkoxy radicals can be alkyl-oxy radicals with the alkyl as defined above, for example, a $C_1$-$C_{10}$ alkyl, such as methoxy, ethoxy, propoxy or butoxy.

The alkoxyalkyl radicals can be $(C_1$-$C_{20})$alkoxy$(C_1$-$C_{20})$ alkyl radicals, such as methoxymethyl, ethoxymethyl, methoxyethyl, ethoxyethyl, and the like.

The cycloalkyl radicals can be $C_4$-$C_8$ cycloalkyl radicals, for example, cyclopentyl and cyclohexyl radicals. The cycloalkyl radicals can be substituted cycloalkyl radicals, such as cycloalkyl radicals substituted by alkyl, alkoxy, carboxylic acid, hydroxyl, amine and/or ketone groups.

The alkyl or alkenyl radicals, when they are optionally substituted, can be substituted by at least one substituent carried by at least one carbon atom chosen from:
a halogen atom;
a hydroxyl group;
a $C_1$-$C_2$ alkoxy radical;
a $C_1$-$C_{10}$ alkoxycarbonyl radical;
a (poly)hydroxy$(C_2$-$C_4)$alkoxy radical;
an amino radical;
a 5- or 6-membered heterocycloalkyl radical;
an optionally cationic 5- or 6-membered heteroaryl radical, such as an imidazolium radical, which is optionally substituted by a $(C_1$-$C_4)$alkyl radical, for example, a methyl radical;
an amino radical substituted by one or two identical or different $C_1$-$C_6$ alkyl radicals optionally carrying at least:
one hydroxyl group,
one amino group optionally substituted by one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other heteroatom other than or the same as nitrogen,
one quaternary ammonium group —N$^+$R'R"R'" M$^-$ for which R', R" and R'", which can be identical or different, represent a hydrogen atom or a $C_1$-$C_4$ alkyl group and M$^-$ represents the counterion of the corresponding organic acid, inorganic acid or halide,
or one optionally cationic 5- or 6-membered heteroaryl radical, such as an imidazolium radical, optionally substituted by a $(C_1$-$C_4)$alkyl radical, for example, a methyl radical;
an acylamino (—NR—COR') radical in which the R radical can be a hydrogen atom or a $C_1$-$C_4$ alkyl radical optionally carrying at least one hydroxyl group and the R' radical is a $C_1$-$C_2$ alkyl radical; a carbamoyl $((R)_2N$—CO—) radical in which the R radicals, which can be identical or different, represent a hydrogen atom or a $C_1$-$C_4$ alkyl radical optionally carrying at least one hydroxyl group; an alkylsulfonylamino (R'SO$_2$—NR—) radical in which the R radical represents a hydrogen atom or a $C_1$-$C_4$ alkyl radical optionally carrying at least one hydroxyl group and the R' radical represents a $C_1$-$C_4$ alkyl radical or a phenyl radical; or an aminosulfonyl $((R)_2N$—SO$_2$—) radical in which the R radicals, which can be identical or different, represent a hydrogen atom or a $C_1$-$C_4$ alkyl radical optionally carrying at least one hydroxyl group, a carboxyl radical in the acid form or salified form (e.g., salified with an alkali metal or a substituted or unsubstituted ammonium);
a cyano group;
a nitro group;
a carboxyl or glycosylcarbonyl group;
a phenylcarbonyloxy group optionally substituted by at least one hydroxyl group;
a glycosyloxy group; and
a phenyl group optionally substituted by at least one hydroxyl group.

The aryl or heterocyclic radicals or the aryl or heterocyclic part of the radicals when they are optionally substituted can be substituted by at least one substituent carried by at least one carbon atom chosen from:
  a $C_1$-$C_{10}$, such as a $C_1$-$C_8$, alkyl radical optionally substituted by at least one radical chosen from the following radicals: hydroxyl, $C_1$-$C_2$ alkoxy, (poly)hydroxy($C_2$-$C_4$)alkoxy, acylamino or amino substituted by two identical or different $C_1$-$C_4$ alkyl radicals, which two radicals optionally carry at least one hydroxyl group or are able to form, with the nitrogen atom to which they are attached, a saturated or unsaturated and optionally substituted 5- to 7-membered, e.g., 5- or 6-membered, heterocycles optionally comprising another heteroatom identical to or different from nitrogen;
  a halogen atom;
  a hydroxyl group;
  a $C_1$-$C_2$ alkoxy radical;
  a $C_1$-$C_{10}$ alkoxycarbonyl radical;
  a (poly)hydroxy($C_2$-$C_4$)alkoxy radical;
  an amino radical;
  a 5- or 6-membered heterocycloalkyl radical;
  an optionally cationic 5- or 6-membered heteroaryl radical, such as an imidazolium radical, which is optionally substituted by a ($C_1$-$C_4$)alkyl radical, for example, a methyl radical;
  an amino radical substituted by one or two identical or different $C_1$-$C_6$ alkyl radicals optionally carrying at least:
    one hydroxyl group,
    one amino group optionally substituted by one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other heteroatom other than or the same as nitrogen,
    one quaternary ammonium group —N$^+$R'R''R''' M$^-$ for which R', R'' and R''', which can be identical or different, represent a hydrogen atom or a $C_1$-$C_4$ alkyl group and M$^-$ represents the counterion of the corresponding organic acid, inorganic acid or halide,
    or one optionally cationic 5- or 6-membered heteroaryl radical, such as an imidazolium radical, optionally substituted by a ($C_1$-$C_4$)alkyl radical, for example, a methyl radical;
  an acylamino (—NR—COR') radical in which the R radical is a hydrogen atom or a $C_1$-$C_4$ alkyl radical optionally carrying at least one hydroxyl group and the R' radical is a $C_1$-$C_2$ alkyl radical; a carbamoyl ((R)$_2$N—CO—) radical in which the R radicals, which can be identical or different, represent a hydrogen atom or a $C_1$-$C_4$ alkyl radical optionally carrying at least one hydroxyl group;
  an alkylsulfonylamino (R'SO$_2$—NR—) radical in which the R radical represents a hydrogen atom or a $C_1$-$C_4$ alkyl radical optionally carrying at least one hydroxyl group and the R' radical represents a $C_1$-$C_4$ alkyl radical or a phenyl radical; or an aminosulfonyl ((R)$_2$N—SO$_2$—) radical in which the R radicals, which can be identical or different, represent a hydrogen atom or a $C_1$-$C_4$ alkyl radical optionally carrying at least one hydroxyl group,
  a carboxyl radical in the acid form or salified form (e.g., salified with an alkali metal or a substituted or unsubstituted ammonium);
  a cyano group;
  a nitro group;
  a polyhaloalkyl group, such as trifluoromethyl;
  a carboxyl or glycosylcarbonyl group;
  a phenylcarbonyloxy group optionally substituted by at least one hydroxyl group;
  a glycosyloxy group; and
  a phenyl group optionally substituted by at least one hydroxyl group.

A "glycosyl radical" is understood to mean a radical resulting from a mono- or polysaccharide.

The radicals comprising at least one silicon atom can in some embodiments be polydimethylsiloxane, polydiphenylsiloxane, polydimethylphenylsiloxane or stearoxy dimethicone radicals.

The heterocyclic radicals can be, for example, radicals comprising, in at least one ring, at least one heteroatom chosen from O, N and S, O or N, which are optionally substituted by a group or groups such as alkyl, alkoxy, carboxylic acid, hydroxyl, amine or ketone groups. These rings can comprise at least one oxo group on the carbon atoms of the heterocycle.

Mention may be made, among the heterocyclic radicals which can be used, of the furyl, pyranyl, pyrrolyl, imidazolyl, pyrazolyl, pyridyl or thienyl groups.

In some embodiments, the heterocyclic groups can be fused groups, such as benzofuranyl, chromenyl, xanthenyl, indolyl, isoindolyl, quinolyl, isoquinolyl, chromanyl, isochromanyl, indolinyl, isoindolinyl, coumarinyl or isocoumarinyl groups, it being possible for these groups to be substituted, e.g., by at least one OH groups.

The ortho-diphenols of use in the method of the disclosure can be natural or synthetic. The natural ortho-diphenols include the compounds which can be present in nature and which can be reproduced by chemical (semi)synthesis.

The salts of the ortho-diphenols of the disclosure can be salts of acids or of bases. The acids can be inorganic or organic acids. In some embodiments, the acid is hydrochloric acid, which results in the chlorides.

The bases can be inorganic or organic bases. In some embodiments, the bases can be alkali metal hydroxides, such as sodium hydroxide, which results in sodium salts.

In some embodiments, the composition comprises, as ingredient i), at least one synthetic ortho-diphenol derivative which does not exist in nature.

In some embodiments, the method for dyeing keratinous fibers employs, as ingredient i), at least one natural ortho-diphenol derivative.

In some embodiments, the at least one ortho-diphenol derivative used in the methods of the disclosure according to i) is chosen from:
  flavanols, such as catechin and epicatechin gallate,
  flavonols, such as quercetin,
  anthocyanidins, such as cyanidin, delphinidin or petunidin,
  anthocyanins or anthocyans, such as myrtillin,
  orthohydroxybenzoates, for example gallic acid salts,
  flavones, such as luteolin,
  hydroxystilbenes, for example 3,3',4,5'-tetrahydroxystilbene, optionally oxylated (for example glucosylated), 3,4-dihydroxyphenylalanine and its derivatives,
2,3-dihydroxyphenylalanine and its derivatives,
4,5-dihydroxyphenylalanine and its derivatives,
dihydroxycinnamates, such as caffeic acid and chlorogenic acid,
orthopolyhydroxycoumarins,
orthopolyhydroxyisocoumarins,
orthopolyhydroxycoumarones,
orthopolyhydroxyisocoumarones,
orthopolyhydroxychalcones,
orthopolyhydroxychromones,
quinones,
hydroxyxanthones,
1,2-dihydroxybenzene and its derivatives,
1,2,4-trihydroxybenzene and its derivatives,
1,2,3-trihydroxybenzene and its derivatives,
2,4,5-trihydroxytoluene and its derivatives,
proanthocyanidins, such as proanthocyanidins A1, A2, B1, B2, B3 and C1,
proanthocyanins,
tannic acid, and
ellagic acid.

When a dyeing precursor exhibits D and L forms, either form can be used in the compositions according to the disclosure, as well as the racemate.

In some embodiments, the natural ortho-diphenols result from extracts of animals, bacteria, fungi, algae or plants used in their entirety or partially. Regarding plants, the extracts can result from plants or plant parts, such as fruits, including citrus fruits, vegetables, trees or bushes. Use may also be made of mixtures of these extracts, rich in ortho-diphenols, as defined above.

In some embodiments, the natural ortho-diphenol or ortho-diphenols of the disclosure result from extracts of plants or of plant parts.

In some embodiments, the extracts can be chosen from:
extracts of tea leaves;
extracts of rosemary leaves;
extracts of mate leaves;
extracts of fruits, such as extracts of grape (e.g., of grape seeds or of grape marc), or
extracts of cocoa beans and/or pods;
extracts of vegetables, such as extracts of onion skins or of salad; and
extracts of tree wood, such as extracts of pine bark, extracts of logwood, extracts of dyer's mulberry (also known as "yellow wood") or extracts of acacia.

Within the meaning of the disclosure, such an extract will be considered a compound i) if it is known to comprise an entity chosen from ortho-diphenol and derivatives thereof.

The extracts can be obtained by extraction of various parts of plants, such as, for example, the root, wood, bark, leaf, flower, fruit, pip, husk or peel.

Mention may be made, among extracts of plants, of extracts of rose or tea leaves, extracts of rosemary leaves or extracts of mate leaves.

Mention may be made, among extracts of fruits, of extracts of apple or of grape (including grape seeds) or extracts of cocoa beans and/or pods.

Mention may be made, among extracts of vegetables, of extracts of potato or of onion skins.

Mention may be made, among extracts of tree wood, of extracts of pine bark or extracts of logwood.

Use may also be made of mixtures of plant extracts.

In some embodiments, the ortho-diphenol derivative or derivatives can be natural extracts rich in ortho-diphenols. In some embodiments, the ortho-diphenol derivative or derivatives are solely natural extracts.

The natural extracts according to the disclosure can be provided in the form of powders or of liquids. In some embodiments, the extracts of the disclosure can be provided in the form of powders.

In some embodiments, the synthetic or natural ortho-diphenol or ortho-diphenol derivative(s) and/or the natural extract(s) used as ingredient i) in at least one composition of use in the methods according to the disclosure can range from 0.001% to 20% by weight of the total weight of the composition or compositions comprising the ortho-diphenol or ortho-diphenols or the extract or extracts.

As regards the pure ortho-diphenols, the content in the composition or compositions comprising them can range, for example, from 0.001% to 5% by weight of each of these compositions.

As regards the extracts, the content in the composition or compositions comprising extracts as is can range, for example, from 0.5% to 20% by weight of each of these compositions.

ii) Metal Salt(s)

The methods of the disclosure use at least one ingredient ii) which is a metal salt.

In some embodiments, the metal salt is a salt of a divalent metal. In some embodiments, the metal salt is a salt of a transition metal. In some embodiments, the metal salt is not a salt of an alkali metal.

In some embodiments, the at least one metal salt is chosen from manganese (Mn) and zinc (Zn) salts.

Within the meaning of the present disclosure, "salt" is understood to include the oxides and hydroxides of these metals and the salts proper that can result from the action of an acid on a metal. In some embodiments, the at least one salt is not an oxide. In some embodiments, the at least one salt is not a hydroxide. Mention may be made, among the salts, of halides, such as chlorides, fluorides and iodides, sulfates, phosphates, nitrates, perchlorates and salts of carboxylic acids and polymeric complexes which can support said salts, and also their mixtures.

In some embodiments, the manganese salt is other than manganese carbonate, manganese hydrogencarbonate or manganese dihydrogencarbonate.

The salts of carboxylic acids which can be used in the disclosure also include salts of hydroxylated carboxylic acids, such as gluconate.

Mention may be made, as example of polymeric complexes which can support said salts, of manganese pyrrolidonecarboxylate.

Mention may be made, as examples, of manganese chloride, manganese fluoride, manganese acetate tetrahydrate, manganese lactate trihydrate, manganese phosphate, manganese iodide, manganese nitrate trihydrate, manganese bromide, manganese perchlorate tetrahydrate, manganese sulfate monohydrate and manganese gluconate. In some embodiments, the at least one salt is chosen from manganese gluconate and manganese chloride. In some embodiments, the at least one salt comprises manganese gluconate and manganese chloride.

Mention may be made, among zinc salts, of zinc sulfate, zinc gluconate, zinc chloride, zinc lactate, zinc acetate, zinc glycinate and zinc aspartate.

The manganese and zinc salts can be introduced in the solid form into the compositions or else can originate from a natural, mineral or thermal, water rich in these ions or also from sea water (for example, Dead Sea water). They can also originate from inorganic compounds, such as earths or ocres, such as clays (for example green clay), or from plant extracts comprising.

In some embodiments, the at least one metal salt of the disclosure has an oxidation state of 2, such as Mn(II) and Zn(II).

In some embodiments, the metal salt or salts used can be present in an amount ranging from 0.001% to 10% by weight of the total weight of the composition(s) comprising this or these metal salts, for example, from 0.05% to 0.1% by weight.

iii) Hydrogen Peroxide or System(s) which Generate(s) Hydrogen Peroxide

In the context of the present disclosure, the third constituent is hydrogen peroxide or at least one system which generate(s) hydrogen peroxide, such as:
 a) urea hydrogen peroxide;
 b) at least one polymeric complex which releases hydrogen peroxide, such as polyvinylpyrrolidone/$H_2O_2$, or other polymeric complexes such as those described in U.S. Pat. Nos. 5,008,093, 3,376,110, and 5,183,901 (in some embodiments, the at least one polymeric complex which releases hydrogen peroxide can be provided in the form of a powder);
 c) at least one oxidase which produces hydrogen peroxide in the presence of an appropriate substrate (for example, glucose in the case of glucose oxidase or uric acid with uricase);
 d) at least one metal peroxide which, in water, generates hydrogen peroxide, such as calcium peroxide or magnesium peroxide;
 e) at least one perborate; or
 f) at least one percarbonate.

In some embodiments, the composition or compositions comprise at least one system which generates hydrogen peroxide, chosen from a) urea hydrogen peroxide; b) at least one polymeric complex which releases hydrogen peroxide, such as polyvinylpyrrolidone/$H_2O_2$; c) at least one oxidase; d) at least one perborate; and e) at least one percarbonate.

In some embodiments, this constituent is hydrogen peroxide.

Furthermore, the composition or compositions comprising the hydrogen peroxide or the least one system which generates hydrogen peroxide can also include at least one of various adjuvants used conventionally in compositions for dyeing the hair, which include those described defined below in part vii).

In some embodiments, the hydrogen peroxide or the at least one system which generates hydrogen peroxide can be present in an amount ranging from 0.001% to 12% by weight, expressed as hydrogen peroxide, with respect to the total weight of the composition or compositions comprising it or them, and more for example, from 0.2% to 2.7% by weight.

In some embodiments, the at least one system which generates hydrogen peroxide does not comprise material that is effervescent as a solid. Materials that are effervescent as a solid include powders and pebbles that can produce bubbling, foaming or liberation of a gas, which can occur, for example, upon contact with a solvent or solution, such as a protic solvent, a solution at acidic pH, or a solution or solvent comprising a free Lewis acid.

iv) (Bi)carbonate(s)

In the context of the present disclosure, the fourth ingredient can be chosen from carbonates and bicarbonates.

Carbonates and bicarbonates (collectively, (bi)carbonates) include:
 a) carbonates of alkali metals ($Met^+_2\ CO_3^{2-}$), of alkaline earth metals ($Met'^{2+}CO_3^{2-}$), of ammonium (($R''_4N^+)_2\ CO_3^{2-}$) or of phosphonium (($R''_4P^+)_2CO_3^{2-}$), with Met' representing an alkaline earth metal and Met representing an alkali metal and R'', which can be identical or different, representing a hydrogen atom or an optionally substituted ($C_1$-$C_6$)alkyl group, such as a hydroxyethyl group, and
 b) bicarbonates, also known as hydrogencarbonates, with the following formulae:
 $R'^+HCO_3^-$, with R' representing a hydrogen atom, an alkali metal or an ammonium $R''_4N^+$ or phosphonium $R''_4P^+$ group, where R'', which can be identical or different, represent a hydrogen atom or an optionally substituted ($C_1$-$C_6$)alkyl group, such as a hydroxyethyl group, and, when R' represents a hydrogen atom, the hydrogencarbonate is then referred to as dihydrogencarbonate ($CO_2$, $H_2O$); and
 $Met'^{2+}(HCO_3^-)_2$, with Met' representing an alkaline earth metal.

In some embodiments, the fourth ingredient is chosen from alkali metal or alkaline earth metal (bi)carbonates, such as alkali metal (bi)carbonates.

Mention may be made of sodium, potassium, magnesium or calcium carbonates or hydrogencarbonates and their mixtures, such as sodium hydrogencarbonate. These hydrogencarbonates can originate from a natural water, for example spring water from the Vichy basin or from La Roche-Posay or Badoit water. In some embodiments, the at least one (bi) carbonate is chosen from sodium carbonate [497-19-8]= $Na_2CO_3$, sodium hydrogencarbonate or sodium bicarbonate [144-55-8]=$NaHCO_3$, and calcium bicarbonate (also known as calcium dihydrogencarbonate)=$Ca(HCO_3)_2$.

According to the disclosure, the (bi)carbonate agent or agents used can be present in an amount ranging from 0.001% to 10% by weight of the total weight of the composition or compositions comprising the (bi)carbonate agent or agents, for example, from 0.005% to 5% by weight.

v) Stage(s) of Mechanical Wiping and/or of Drying and/or Non Rinsing:

The methods for dyeing keratinous fibers according to the disclosure comprise at least one intermediate stage of mechanical wiping of the fibers and/or of drying and/or non rinsing of the fibers.

The mechanical wiping and drying stages are also called "controlled leave-in" stages, which differ from a "rinse-out" stage performed under an intense water jet, and from a "non rinsing" or "leave in" procedure, in which there is immediate progression from the first to the second stage of development.

Mechanical wiping of the fibers is understood to mean the rubbing of an absorbent item over the fibers and the physical withdrawal, via the absorbent item, of the surplus of ingredient(s) which has/have not penetrated into the fibers. The absorbent item can be a piece of cloth, such as a towel, e.g., a terry towel, a dish towel, or paper towel or other absorbent paper.

In some embodiments, the mechanical wiping is performed in a way that leaves the keratinous fibers wet, i.e., the wiping does not cause total drying of the keratinous fibers.

Drying is understood to mean the action of evaporating the organic solvents and/or water occurring in one or more compositions used in the methods of the disclosure, comprising or not comprising one or more ingredients i) to iv) as defined above. Drying can be carried out via a heat source (convection, conduction or radiation) by sending, for example, a hot gas stream, such as air, which promotes the evaporation of the solvent or solvents. Mention may be made, as heat source, of a hair dryer, including hood hair dryers, an iron for smoothing the hair, a dispenser of infrared rays, and any other conventional heating device.

vi) Water:

In some embodiments, water is used in the method of the disclosure. It can be provided by wetting of the keratinous fibers and/or as part of the composition or compositions comprising the compounds i) to iv) as defined above, and/or from at least one other composition. In some embodiments, the water originates at least from a composition comprising at least one compound chosen from i) to iv) as defined above.

In some embodiments, at least one of the at least one ortho-diphenol derivative, the at least one metal salt, the hydrogen peroxide or at least one system which generates hydrogen peroxide, or the at least one (bi)carbonate is applied to keratinous fibers in a composition comprising water in an amount greater than or equal to 50%, 60%, 70%, 80%, 90%, 91%, 92%, 93%, 94%, 95%, 96%, 97%, or 98% by weight of the total weight of the composition. In some embodiments, at least one of the at least one ortho-diphenol derivative, the at least one metal salt, the hydrogen peroxide or at least one system which generates hydrogen peroxide, or the at least one (bi)carbonate is applied to keratinous fibers in a composition comprising water in an amount ranging from 50% to 98%; from 60% to 97%; from 70% to 96%; from 80% to 95%; from 90% to 95%; from 60% to 97%; from 70% to 96%; from 80% to 95%; or from 90% to 95%.

In some embodiments, the cosmetic compositions according to the disclosure comprise at least one ortho-diphenol derivative; at least one metal salt; hydrogen peroxide or at least one system which generates hydrogen peroxide; at least one (bi)carbonate, and water, wherein the water is present in an amount greater than or equal to 50%, 60%, 70%, 80%, 90%, 91%, 92%, 93%, 94%, 95%, 96%, 97%, or 98% by weight of the total weight of the cosmetic composition. In some embodiments, the cosmetic compositions according to the disclosure comprise at least one ortho-diphenol derivative; at least one metal salt; hydrogen peroxide or at least one system which generates hydrogen peroxide; at least one (bi) carbonate, and water, wherein the water is present in an amount ranging from 50% to 98%; from 60% to 97%; from 70% to 96%; from 80% to 95%; from 90% to 95%; from 60% to 97%; from 70% to 96%; from 80% to 95%; or from 90% to 95%.

In some embodiments, the multicompartment devices according to the disclosure comprise from 2 to 5 compartments comprising from 2 to 5 compositions which collectively comprise at least one ortho-diphenol derivative; at least one metal salt; hydrogen peroxide or at least one system which generates hydrogen peroxide; at least one (bi)carbonate; and water, said 2 to 5 compositions being aqueous or pulverulent, with at least one of these compositions being aqueous, wherein water is present in the 2 to 5 compositions in a total amount greater than or equal to 50%, 60%, 70%, 80%, 90%, 91%, 92%, 93%, 94%, 95%, 96%, 97%, or 98% by weight of the total weight of the 2 to 5 compositions.

In some embodiments, the multicompartment devices according to the disclosure comprise from 2 to 5 compartments comprising from 2 to 5 compositions which collectively comprise at least one ortho-diphenol derivative; at least one metal salt; hydrogen peroxide or at least one system which generates hydrogen peroxide; at least one (bi)carbonate; and water, said 2 to 5 compositions being aqueous or pulverulent, with at least one of these compositions being aqueous, wherein water is present in the 2 to 5 compositions in a total amount ranging from 50% to 98%; from 60% to 97%; from 70% to 96%; from 80% to 95%; from 90% to 95%; from 60% to 97%; from 70% to 96%; from 80% to 95%; or from 90% to 95%.

In some embodiments, said 2 to 5 compositions can be aqueous or pulverulent, with at least one of these compositions being aqueous, wherein water is present in the 2 to 5 compositions in a total amount greater than or equal to 50% by weight of the total weight of the 2 to 5 compositions.

vii) Cosmetic Compositions:

The ingredients i) to iv) can occur alone or in a cosmetic composition. The cosmetic compositions used in the method according to the disclosure can comprise a cosmetically acceptable dyeing vehicle, such as a dyeing vehicle comprising water, a mixture of water and of at least one organic solvent, or at least one organic solvent.

The term "organic solvent" is understood to mean an organic substance capable of dissolving or dispersing another substance without modifying it chemically.

In some embodiments, the cosmetic dyeing compositions according to the disclosure comprise water.

In some embodiments, the cosmetic compositions according to the disclosure comprise i) at least one entity chosen from ortho-diphenol and derivatives thereof, ii) at least one metal salt, iii) hydrogen peroxide or at least one system which generates hydrogen peroxide, and iv) at least one (bi)carbonate, wherein the ingredients i) through iv) are mutually different, i.e., one entity or chemical species does not serve as two of the ingredients i) through iv).

The Organic Solvents:

Mention may be made, as organic solvents, for example, of lower $C_1$-$C_4$ alkanols, such as ethanol and isopropanol, polyols and polyol ethers, such as 2-butoxyethanol, propylene glycol, propylene glycol monomethyl ether, diethylene glycol monoethyl ether, diethylene glycol monomethyl ether or hexylene glycol, and aromatic alcohols, such as benzyl alcohol or phenoxyethanol.

The organic solvent(s) can be present in an amount ranging from 1% to 40% by weight, with respect to the total weight of the dyeing composition, or from 5% to 30% by weight.

The Adjuvants:

The composition or compositions of the dyeing method in accordance with the disclosure can also include various adjuvants conventionally used in compositions for dyeing the hair, which can be chosen from anionic, nonionic, cationic, amphoteric or zwitterionic surface-active agents or their mixtures, anionic polymers other than surfactants, cationic, nonionic, amphoteric or zwitterionic polymers or their blends, inorganic or organic thickening agents, such as anionic, cationic, nonionic and amphoteric polymeric associative thickeners, antioxidants, penetration agents, sequestering agents, fragrances, buffers, dispersing agents, conditioning agents, such as, for example, volatile or nonvolatile and modified or unmodified silicones, film-forming agents, ceramides, preservatives and opacifying agents.

Said adjuvants can be chosen from surface-active agents, such as anionic or nonionic surfactants or their mixtures, and inorganic or organic thickening agents.

The above adjuvant or adjuvants can be present in an amount, for each of them, ranging from 0.01% to 40% by weight, with respect to the weight of the composition or compositions comprising the ingredients i) to iv) as defined above, for example, from 0.1% to 20% by weight, with respect to the weight of the composition.

Of course, a person skilled in the art will take care to choose the optional additional compound or compounds so that the beneficial properties of the at least one composition of use in the coloring method in accordance with the disclosure are not, or not substantially, detrimentally affected by the envisaged addition or additions.

The Additional Dyes:

The method employing the ingredients i) to iv) as defined above can in addition employ or comprise at least one direct dye. These direct dyes can be, for example, chosen from those conventionally used in direct dyeing, among which may be mentioned any of the aromatic and/or nonaromatic dyes commonly used, such as neutral, acid or cationic nitrobenzene direct dyes, neutral, acid or cationic azo direct dyes, natural direct dyes other than ortho-diphenols, neutral, acid or cationic quinones such as anthraquinone direct dyes, azine, triarylmethane or indoamine direct dyes, methines, styryls, porphyrins, metalloporphyrins, phthalocyanines, methinecyanines and fluorescent dyes.

Mention may be made, among natural direct dyes, of lawsone, juglone, indigo, isatin, curcumin, spinulosin, apigenidine or orceins. Use may also be made of extracts or decoctions comprising these natural dyes such as cataplasms or henna-based extracts.

The additional direct dye or dyes used in the composition or compositions comprising the ingredients 0 to iv) used in the method according to the disclosure can range from 0.001% to 10% by weight of the total weight of the composition or compositions comprising them, for example, 0.05% to 5% by weight.

The compositions of the method employing the ingredients i) to iv) as defined above can also employ at least one oxidation base and/or at least one coupler conventionally used for the dyeing of keratinous fibers.

Mention may be made, among the oxidation bases, of para-phenylenediamines, bisphenylalkylenediamines, para-aminophenols, bis-para-aminophenols, ortho-aminophenols, heterocyclic bases and their addition salts.

Mention may be made, among these couplers, of meta-phenylenediamines, meta-aminophenols, meta-diphenols, naphthalene couplers, heterocyclic couplers and their addition salts.

The oxidation base or bases present in the composition or compositions can be present each in an amount ranging from 0.001% to 10% by weight of the total weight of the corresponding composition or compositions.

The cosmetic composition(s) used in the method of the disclosure can be provided in various formulation forms, such as a powder, a lotion, a foam, a cream or a gel, or in any other form appropriate for carrying out dyeing of keratinous fibers. It can also be packaged as a propellant-free pump-action spray or under pressure in an aerosol container in the presence of a propellant and form a foam.

pH of the Composition(s) of the Method

In some embodiments, the pH of the composition or compositions of the method comprising the (bi)carbonate or (bi)carbonates is greater than 7; in some embodiments, said pH ranges from 8 to 12, e.g., from 8 to 10.

The pH of the composition or compositions comprising the hydrogen peroxide or a system which generates hydrogen peroxide can in some embodiments have a pH less than 7, e.g., a pH ranging from 1 to 5, such as if the composition or compositions do not comprise (bi)carbonates.

In some embodiments, the composition or compositions comprising the ortho-diphenol or ortho-diphenols of the disclosure and not comprising (bi)carbonates can be at a pH of less than 7, e.g., a pH ranging from 3 to 6.5.

According to a form of the method of the disclosure, the compositions comprising the metal salt or salts and not comprising (bi)carbonates can be at a pH of less than 7, e.g., a pH ranging from 3 to 6.5.

The pH of these compositions can be adjusted to the desired value using an acidifying or basifying agent or agents commonly used in the dyeing of keratinous fibers and/or using a conventional buffer system or systems.

Mention may be made, among the acidifying agents of the compositions used in the disclosure, by way of example, of inorganic or organic acids, such as hydrochloric acid, orthophosphoric acid, sulfuric acid, carboxylic acids, such as acetic acid, tartaric acid, citric acid or lactic acid, or sulfonic acids.

In some embodiments, a basifying agent is added to at least one of the compositions of the dyeing method comprising the (bi)carbonate or (bi)carbonates. This basic agent can be chosen from aqueous ammonia, alkali metal carbonates, alkanolamines, such as mono-, di- and triethanolamines, and their derivatives, sodium hydroxide, potassium hydroxide and the compounds of formula (II):

(II)

in which W is a propylene residue optionally substituted by a hydroxyl group or a $C_1$-$C_4$ alkyl radical and $R_a$, $R_b$, $R_c$ and $R_d$, which can be identical or different, represent a hydrogen atom, a $C_1$-$C_4$ alkyl radical or a $C_1$-$C_4$ hydroxyalkyl radical.

viii) Multistage Coloring Method

In some embodiments, the method for dyeing keratinous fibers consists of, or consists essentially of:
a) in a first stage, treating said fibers with:
  i) at least one entity chosen from ortho-diphenol and derivatives thereof,
  ii) at least one metal salt, such as manganese and zinc salts, and
  iii) hydrogen peroxide or at least one system which generates hydrogen peroxide,
the ingredients i) to iii) being applied to said fibers together or separately;
b) in a second stage, at least one of wiping the fibers mechanically, drying the fibers, or not rinsing the fibers; and
c) in a third stage, treating said fibers with iv) at least one (bi)carbonate.

According to another embodiment of the disclosure, the method for dyeing keratinous fibers consists of, or consists essentially of:
a) in a first stage, treating said fibers with:
  i) at least one entity chosen from ortho-diphenol and derivatives thereof, and
  ii) at least one metal salt, such as manganese and zinc salts,
b) in a second stage, at least one of wiping the fibers mechanically, drying the fibers, or not rinsing the fibers; and
c) in a third stage, treating said fibers with iii) hydrogen peroxide or at least one system which generates hydrogen peroxide and iv) at least one (bi)carbonate;
it being understood that the ingredients i) and ii) can be applied to said fibers together or separately, and it being understood that the ingredients iii) and iv) can be applied to said fibers together or separately.

The keratinous fibers may or may not be wetted beforehand.

In the second stage, said fibers can be wiped mechanically once or a series of times to remove excess material comprising ingredients i) and ii) or ingredients i), ii) and iii).

In the second stage, if the drying method is thermal, for example via a hair dryer, including a hood hair dryer, or smoothing iron or in the open air, then the fibers can be dried until the wet appearance of the hair has disappeared visually. For example, the keratinous fibers can be dried using a smoothing iron or a hair dryer.

The leave-in time after application is in some embodiments a time ranging from 3 to 120 minutes, such as from 10 to 60 minutes or from 15 to 45 minutes.

At least one successive or non-successive wiping and/or drying operation can be envisaged between the applications of ingredients i) and ii), or between each of the applications of ingredients i), ii) and iii), or between each of the applications of ingredients i), ii), iii) and iv), or between the applications of the mixture of i) and ii) and of the mixture of iii) and iv), or between the applications of the mixture of i) and ii), of the ingredient iii), and of the ingredient iv).

The wiping and/or drying stage can be carried out after application of the mixture of ingredients i), ii), and iii) as defined above, and before the application of the ingredient iv).

The method can involve at least one successive stage of wiping after the application of the mixture of ingredients i), ii), and iii). In this case, the wiping sequence can be carried out until the excess of said mixture has disappeared visually and the fibers have dried.

The leave-in time after application of each of the ingredients or of the mixtures range from 3 to 120 minutes, such as from 3 to 60 minutes, or from 5 to 30 minutes.

Whatever the method of application, the application temperature can range from ambient temperature (ambient temperature ranging from about 15 to about 25° C.) to 80° C., such as from 15 to 45° C. Thus, in some embodiments, after application of the composition or compositions according to the disclosure, the hair can be subjected to a heat treatment by heating at a temperature ranging from 30 to 60° C. In practice, this operation can be carried out using a hair styling hood, a hair dryer, a dispenser of infrared rays, or any other conventional heating device.

When, in the method, a thermal heating device such as a heating iron is used, its temperature can range from 60 to 220° C. such as from 120 to 200° C.

In some embodiments, the coloring method is carried out at ambient temperature (25° C.) during the application of the ingredients i) to iv).

In all the embodiments of the methods described above, it is possible for the compositions mentioned to be ready-for-use compositions such as result from the mixing, at the time of use, of at least two compositions, which can be compositions provided in a dyeing kit or kits.

By way of non-limiting illustration, concrete examples of certain embodiments of the present disclosure are given below. The examples that follow serve to illustrate the invention without, however, being limiting in nature.

I) DYEING EXAMPLES

The following composition was prepared:

| Composition A | A |
|---|---|
| Catechin | 5 g |
| Pine bark extract | — |

-continued

| Composition A | A |
|---|---|
| Hexylene glycol | 5 g |
| Sodium lauryl ether sulfate (70% as AM in water) | 3.75 g |
| Manganese gluconate (i.e. 0.01% by weight of $Mn^{2+}$ metal equivalent) | 0.081 g |
| Hydrogen peroxide | 1.2 g |
| Citric acid or sodium hydroxide | q.s. for pH 5 |
| Demineralized water | q.s. for 100 g |

The composition A was applied to locks of dry natural hair comprising 90% white hairs, and to dry permed hair comprising 90% white hairs, with a bath ratio of 5 g of formulation per 1 g of hair. The treated hair was subsequently left to develop at a temperature of 50° C. for 30 minutes.

At the end, the hair impregnated with the first composition was wiped using an absorbent towel in order to remove the excess formulation.

| Composition B | B |
|---|---|
| Sodium bicarbonate $NaHCO_3$ | 5 g |
| Carbomer | 1 g |
| Monoethanolamine | q.s. for pH 9 |
| Demineralized water | q.s. for 100 g |

The composition B was subsequently applied to the hair with a bath ratio of 4 g per 1 g of lock; the development time was 10 minutes at ambient temperature. After a few minutes, a very intense coloring appeared.

After the locks were rinsed, shampooed and dried under a hood, the hair was subsequently rinsed with water, washed with a conventional shampoo and dried under a hood.

The coloring was very persistent toward washing operations and light.

Colorimetric Results:

The coloring of the hair was evaluated visually and read on a Minolta spectrocolorimeter (CM3600d, illuminant D65, angle 10°, SCI values) for the L*, a*, b* colorimetric measurements.

In this L*, a*, b* system, L* represents the intensity of the color, a* indicates the green/red color axis and b* indicates the blue/yellow color axis. The lower the value of L, the darker or more intense the color. The higher the value of a*, the redder the shade; the higher the value of b*, the yellower the shade.

a) The variation in coloring between the colored locks of natural white hair which is untreated (control) and natural white hair after perm treatment are defined by $\Delta E^*$ according to the following equation:

$$\Delta E^* = \sqrt{(L^* - L_o^*)^2 + (a^* - a_o^*)^2 + (b^* - b_o^*)^2}$$

In this equation, L*, a* and b* represent the values measured after dyeing the natural/permed hair comprising 90% white hairs and $L_o^*$, $a_o^*$ and $b_o^*$ represent the values measured for the untreated natural/permed hair comprising 90% white hairs.

The greater the value of ΔE, the greater the difference in color between the control locks and the treated locks.

b) The variation in coloring between the natural locks white hair treated (NW) and natural permed white hair treated (PW) was defined by the selectivity $\Delta E_{selec}$, which corresponds to the difference between the keratin fibers from the root (natural, i.e., without permanent treatment) to the tip (permanent treatment) according to the following equation:

$$\Delta E_{selec} = \sqrt{(L-L_o)^2 + (a-a_0)^2 + (b-b_0)^2}$$

In this equation, L, a and b represent the values measured after dyeing the permed hair comprising 90% white hairs and $L_0$, $a_0$ and $b_0$ represent the values measured after dyeing the natural hair comprising 90% white hairs.

The greater the value of $\Delta E_{selec}$, the greater the difference in color between the root and the tip and the greater is the non-homogeneity of the color.

Chromaticity: C*

Chromaticity in the CIE L*, a*, b* colorimetric system is calculated according to the following equation:

$$C^* = \sqrt{a^{*2} + b^{*2}}$$

The greater the value of C*, the greater the chromaticity is.

II) COMPARATIVE EXAMPLES

Dyeing Method

In order to demonstrate the performance in terms of dyeing the hair using the method according to the disclosure, three comparative examples of methods in RINSE-OUT, CONTROLLED LEAVE-IN and LEAVE-IN forms were carried out.

RINSE-OUT: intermediate rinsing of the locks with faucet water.

LEAVE-IN: immediate progression to the second stage of development.

CONTROLLED LEAVE-IN: wiping, using an absorbent towel, of the locks of hair impregnated with lotion. An alternative form also consists in drying the hair after the stage of wiping or superficially drying.

| | Examples (on natural hair comprising 90% of white hairs) | | | | |
|---|---|---|---|---|---|
| | Control (untreated hair) | 1 comparative | 2 disclosure | 3 disclosure | 4 disclosure |
| Composition A Stage 1 | — | A | A | A | A |
| Intermediate stage | — | Rinsing | Wiped wet | Wiped dried | Leave-in |
| Composition B Stage 2 | — | B | B | B | B |
| Shades on hair | — | very light golden | very intense coppery | very intense coppery | very intense coppery |
| L* | 54.88 | 51.66 | 37.92 | 39.39 | 40.11 |
| a* | 0.87 | 5.54 | 13.38 | 13.35 | 14.51 |
| b* | 12.33 | 21.85 | 25.31 | 26.4 | 28.13 |
| ΔE | — | 11.09 | 24.75 | 24.37 | 25.58 |
| ΔL* | — | −3.22 | −16.96 | −15.49 | −14.77 |
| Δa* | — | 4.67 | 12.51 | 12.48 | 13.63 |
| Δb* | — | 9.53 | 12.98 | 14.07 | 15.81 |

| | Examples (on permed natural hair comprising 90% of white hairs) | | | | |
|---|---|---|---|---|---|
| | Control (untreated hair) | 5 comparative | 6 disclosure | 7 disclosure | 8 disclosure |
| Composition A Stage 1 | — | A | A | A | A |
| Intermediate stage | — | Rinsing | Wiped wet | Wiped dried | Leave-in |
| Composition B Stage 2 | — | B | B | B | B |
| Shades on hair | — | very light golden green | very intense coppery | very intense coppery | very intense coppery |
| L* | 56.59 | 44.83 | 39.18 | 33.96 | 35.02 |
| a* | 0.74 | 2.71 | 15.04 | 14.05 | 12.13 |
| b* | 13.83 | 19.38 | 29.37 | 23.34 | 23.77 |
| ΔE | — | 13.15 | 27.37 | 27.93 | 26.35 |
| ΔL* | — | −11.76 | −17.41 | −22.63 | −21.57 |
| Δa* | — | 1.98 | 14.31 | 13.31 | 11.4 |
| Δb* | — | 5.55 | 15.54 | 9.51 | 9.94 |

It is apparent from the above tables that the locks of natural or permed white hair treated with the method which involves at least one wiping or drying stage according to the disclosure made it possible to dye in a significantly more chromatic way than the method according to the comparison test. Furthermore, the methods according to the disclosure provide the hair with a much more intense color than those obtained in the comparison tests ($L^*$ was lower with the compositions according to the disclosure).

The following composition was prepared:

| Composition A' | A1 |
|---|---|
| Catechin | 4 g |
| Hexylene glycol | 5 g |
| Sodium lauryl ether sulfate (70% as AM in water) | 3.75 g |
| Manganese gluconate (i.e. 0.01% by weight of $Mn^{2+}$ metal equivalent) | 0.036 g |
| Hydrogen peroxide | 1.2 g |
| Citric acid or sodium hydroxide | qsp pH 5 |
| Demineralized water | qsp 100 g |

The composition A' was applied to locks of dry natural hair comprising 90% white hairs and to dry permed hair comprising 90% white hairs with a bath ratio of 5 g of formulation per 1 g of hair. The treated hair was subsequently left to develop at a temperature of 50° C. for 30 minutes.

The hair impregnated with the first composition was then wiped using an absorbent towel in order to remove the excess formulation.

| Composition B' | B'1 |
|---|---|
| Sodium bicarbonate $NaHCO_3$ | 2.6 g |
| Monoethanolamine or citric acid | qsp pH 9 |
| Demineralized water | qsp 100 g |

The composition B' was subsequently applied to the hair with a bath ratio of 4 g per 1 g of lock; the development time was 10 minutes at ambient temperature. After a few minutes, a very intense coloring appears.

After the locks have been rinsed, shampooed and dried under a hood, the hair was subsequently rinsed with water, washed with a conventional shampoo and dried under a hood.

The coloring was very persistent toward washing operations and light.

| | Example (on natural hair comprising 90% of white hairs) 9 |
|---|---|
| Composition (A'i) Stage 1 | A'1 |
| Intermediate stage | Non rinsed, wiped |
| Composition (B'i) Stage 2 | B'1 |
| Shades on hair | coppery |
| Chromaticity (C*) | 34.30 |

| | Example (on permed natural hair comprising 90% of white hairs) 9 |
|---|---|
| Composition (A'i) Stage 1 | A'1 |
| Intermediate stage | Non rinsed, wiped |
| Composition (B'i) Stage 2 | B'1 |
| Shades on hair | coppery |
| Chromaticity (C*) | 34.96 |

| | Example (on natural hair comprising 90% of white hairs) Comparative 10 |
|---|---|
| Composition (A'i) Stage 1 | A'1 |
| Intermediate stage | Rinsed, wiped |
| Composition (B'i) Stage 2 | B'1 |
| Shades on hair | golden green |
| Chromaticity (C*) | 30.18 |

| | Example (on permed natural hair comprising 90% of white hairs) Comparative 10 |
|---|---|
| Composition (A'i) Stage 1 | A'1 |
| Intermediate Stage | Rinsed, wiped |
| Composition (B'i) Stage 2 | B'1 |
| Shades on hair | golden green |
| Chromaticity (C*) | 29.77 |

Selectivity

| | |
|---|---|
| Selectivity $\Delta E_{selec}$ (NW/PW) NON RINSED + WIPED (Example 9) | 1.08 |
| Selectivity $\Delta E_{selec}$ (NW/PW) RINSED + WIPED (comparative example 10) | 6.08 |

Keratinous fibers dyed with the method for dyeing keratinous fibers according to the disclosure carrying out a non-rinsed stage were observed to have coloration significantly more homogeneous than the fibers dyed with the comparative method having a rinse stage just before application of ingredient iv), since selectivity ($\Delta E_{selec}$) was significantly lower). Moreover, the method for dyeing keratinous fibers according to the disclosure (see example 9) allowed the coloration of the fibers with significantly more chromaticity than the comparative (see example 10), on natural hair as well as permed hair.

What is claimed is:

1. A multistage method for dyeing keratinous fibers, comprising:
    a) treating said fibers, in at least two stages, with:
        i) at least one entity chosen from ortho-diphenol and derivatives thereof,
        ii) at least one metal salt,
        iii) hydrogen peroxide or at least one system which generates hydrogen peroxide, and
        iv) at least one (bi)carbonate; and
    b) at least one of mechanically wiping or drying the fibers, wherein the mechanical wiping or drying occurs between the first and last of the at least two treating stages, with the proviso that said method does not comprise a rinsing stage just before the stage of treating the fibers with the at least one (bi)carbonate.

2. The dyeing method of claim 1, wherein the at least one entity is chosen from natural ortho-diphenol derivatives.

3. The dyeing method of claim 1, in which the at least one entity is an ortho-diphenol or derivative thereof comprising an aromatic ring chosen from benzene, naphthalene, tetrahydronaphthalene, indane, indene, anthracene, phenanthrene, isoindole, indoline, isoindoline, benzofuran, dihydrobenzofuran, chromane, isochromane, chromene, isochromene, quinoline, tetrahydroquinoline and isoquinoline, said aromatic ring comprising at least two hydroxyl groups carried by two contiguous adjacent atoms of the aromatic ring.

4. The dyeing method of claim 1, in which the at least one entity is chosen from entities of formula (I), oligomers thereof, and salified forms thereof:

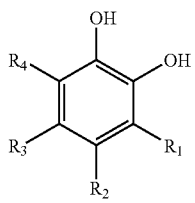

(I)

in which formula (I):
R$_1$ to R$_4$, which are identical or different, represent substituents chosen from:
a hydrogen atom,
a halogen atom,
a hydroxyl radical,
a carboxyl radical,
an alkyl carboxylate or alkoxycarbonyl radical,
an optionally substituted amino radical,
an optionally substituted linear or branched alkyl radical,
an optionally substituted linear or branched alkenyl radical,
an optionally substituted cycloalkyl radical,
an alkoxy radical,
an alkoxyalkyl radical,
an alkoxyaryl radical, it being possible for the aryl group to be optionally substituted,
an aryl radical,
a substituted aryl radical,
a saturated or unsaturated heterocyclic radical which does or does not carry a cationic or anionic charge, which is optionally substituted and/or which is optionally fused with an aromatic ring, said aromatic ring being optionally substituted, and
a radical comprising at least one silicon atom;
except that, two of the adjacent substituents R$_1$-R$_2$, R$_2$-R$_3$ or R$_3$-R$_4$ can jointly form a saturated or unsaturated, aromatic or nonaromatic and substituted or unsubstituted ring optionally comprising at least one heteroatom and optionally fused with at least one saturated or unsaturated and optionally substituted ring optionally comprising at least one heteroatom.

5. The dyeing method of claim 4, in which the at least one entity is chosen from:
flavonols,
anthocyanidins,
anthocyanins or anthocyans,
orthohydroxybenzoates,
flavones,
hydroxystilbenes,
3,4-dihydroxyphenylalanine or a derivative thereof,
2,3-dihydroxyphenylalanine or a derivative thereof,
4,5-dihydroxyphenylalanine or a derivative thereof,
dihydroxycinnamates,
orthopolyhydroxycoumarins,
orthopolyhydroxyisocoumarins,
orthopolyhydroxycoumarones,
orthopolyhydroxyisocoumarones,
orthopolyhydroxychalcones,
orthopolyhydroxychromones,
orthopolyhydroxyquinones,
orthohydroxyxanthones,
1,2-dihydroxybenzene or a derivative thereof,
1,2,4-trihydroxybenzene or a derivative thereof,
1,2,3-trihydroxybenzene or a derivative thereof,
2,4,5-trihydroxytoluene or a derivative thereof,
proanthocyanidins,
proanthocyanins,
tannic acid, and
ellagic acid.

6. The dyeing method of claim 2, wherein the at least one natural ortho-diphenol derivative is chosen from natural ortho-diphenol derivatives present in at least one extract of animals, bacteria, fungi, algae and plants.

7. The dyeing method of claim 6, wherein the at least one extract of an animal, bacterium, fungus, alga or plant is chosen from:
extracts of tea leaves,
extracts of rosemary leaves,
extracts of mate leaves,
extracts of fruits,
extracts of cocoa beans and/or pods,
extracts of vegetables, and
extracts of tree wood.

8. The dyeing method of claim 7, wherein the at least one extract is chosen from:
extracts of grape,
extracts of onion skins,
extracts of salad,
extracts of dyer's mulberry, and
extracts of acacia.

9. The dyeing method of claim 1, in which the at least one metal salt is chosen from manganese and zinc oxides.

10. The dyeing method of claim 1, in which the at least one metal salt is chosen from manganese halides, sulfates, phosphates, nitrates, perchlorates, and salts of carboxylic acids, and zinc halides, sulfates, phosphates, nitrates perchlorates, and salts of carboxylic acids.

11. The dyeing method of claim 1, in which the hydrogen peroxide or at least one system which generates hydrogen peroxide is chosen from hydrogen peroxide and urea hydrogen peroxide.

12. The dyeing method of claim 1, in which the at least one (bi)carbonate is chosen from alkali metal (bi)carbonates and alkaline earth metal (bi)carbonates.

13. The dyeing method of claim 1, wherein the method consists of:
a) in a first stage, treating said fibers with one to three compositions collectively comprising:
i) the at least one entity chosen from ortho-diphenol and derivatives thereof,
ii) the at least one metal salt, and
iii) the hydrogen peroxide or at least one system which generates hydrogen peroxide,
b) in a second stage, performing at least one of mechanically wiping said fibers and drying said fibers, and c) in a third stage, treating said fibers with iv) at least one (bi)carbonate.

14. The dyeing method of claim 1, wherein the method consists of:
   a) in a first step, treating said fibers with, together or separately:
      i) the at least one entity chosen from ortho-diphenol and derivatives thereof, and
      ii) the at least one metal salt,
   b) in a second stage, performing at least one of mechanically wiping said fibers or drying said fibers, and
   c) in a third stage, treating said fibers with, together or separately iii) the hydrogen peroxide or the at least one system which generates hydrogen peroxide and iv) at least one (bi)carbonate.

15. The dyeing method of claim 1, wherein stage b) of the method comprises drying the keratinous fibers using heat.

16. A multistage method for dyeing keratinous fibers, comprising:
   a) treating said fibers, in at least two stages, with:
      i) at least one entity chosen from ortho-diphenol and derivatives thereof,
      ii) at least one metal salt,
      iii) hydrogen peroxide or at least one system which generates hydrogen peroxide, and
      iv) at least one (bi)carbonate; and
   b) mechanically wiping the keratinous fibers to remove excess material, at least once between the first and last of the at least two treating stages, said mechanical wiping occurring either after treating the fibers with ingredients i) and ii) and said excess material comprising ingredients i) and ii), or after treating the fibers with ingredients i), ii), and iii), and said excess material comprising ingredients i), ii), and iii), with the proviso that said method does not comprise a rinsing stage just before the stage of treating the fibers with the at least one (bi)carbonate.

17. The dyeing method of claim 16, wherein stage b) of the method further comprises drying the keratinous fibers using heat.

* * * * *

UNITED STATES PATENT AND TRADEMARK OFFICE
CERTIFICATE OF CORRECTION

PATENT NO.         : 7,857,866 B2
APPLICATION NO.    : 12/637264
DATED              : December 28, 2010
INVENTOR(S)        : Frédéric Guerin Page 1 of 1

It is certified that error appears in the above-identified patent and that said Letters Patent is hereby corrected as shown below:

On the Title Page, Item (54), in the Title, lines 3-4, "NON RINSING" should read --NONRINSING--.

On the Title Page, Item (30), in the "Foreign Application Priority Data", "08 58554" should read --0858554--.

On the Title Page, Item (57), in the Abstract, line 2, "at least entity" should read --at least one entity--.

On the Title Page, Item (57), in the Abstract, line 7, "non rinsing" should read --nonrinsing--.

In claim 7, column 22, line 31, "mate" should read --maté--.

In claim 10, column 22, line 48, "nitrates perchlorates," should read --nitrates, perchlorates,--.

Signed and Sealed this
Twenty-fourth Day of May, 2011

David J. Kappos
*Director of the United States Patent and Trademark Office*

UNITED STATES PATENT AND TRADEMARK OFFICE
CERTIFICATE OF CORRECTION

PATENT NO. : 7,857,866 B2  
APPLICATION NO. : 12/637264  
DATED : December 28, 2010  
INVENTOR(S) : Frédéric Guerin Page 1 of 1

It is certified that error appears in the above-identified patent and that said Letters Patent is hereby corrected as shown below:

On the Title Page, Item (54) and at Column 1, lines 3-4, in the Title, "NON RINSING" should read --NONRINSING--.

On the Title Page, Item (30), in the "Foreign Application Priority Data", "08 58554" should read --0858554--.

On the Title Page, Item (57), in the Abstract, line 2, "at least entity" should read --at least one entity--.

On the Title Page, Item (57), in the Abstract, line 7, "non rinsing" should read --nonrinsing--.

In claim 7, column 22, line 31, "mate" should read --maté--.

In claim 10, column 22, line 48, "nitrates perchlorates," should read --nitrates, perchlorates,--.

This certificate supersedes the Certificate of Correction issued March 24, 2011.

Signed and Sealed this  
Twenty-first Day of June, 2011

David J. Kappos  
*Director of the United States Patent and Trademark Office*